(12) United States Patent
Mehdizadeh et al.

(10) Patent No.: US 8,843,200 B2
(45) Date of Patent: Sep. 23, 2014

(54) NEUROLOGICAL SCREENING CONNECTOR

(75) Inventors: Bruce R. Mehdizadeh, Savage, MN (US); Farook M. Francis, St. Paul, MN (US); Jonathan P. Dorff, Fridley, MN (US); Alyse R. Stofer, Cottage Grove, MN (US)

(73) Assignee: Medtronic, Inc., Minneapolis, MN (US)

( * ) Notice: Subject to any disclaimer, the term of this patent is extended or adjusted under 35 U.S.C. 154(b) by 176 days.

(21) Appl. No.: 13/088,525

(22) Filed: Apr. 18, 2011

(65) Prior Publication Data

US 2011/0270068 A1 Nov. 3, 2011

Related U.S. Application Data

(60) Provisional application No. 61/329,261, filed on Apr. 29, 2010.

(51) Int. Cl.
*A61N 1/00* (2006.01)
*A61N 1/375* (2006.01)
*A61N 1/05* (2006.01)

(52) U.S. Cl.
CPC ............. *A61N 1/3752* (2013.01); *A61N 1/0551* (2013.01)
USPC .......................................................... 607/35

(58) Field of Classification Search
CPC ... A61N 1/375; A61N 1/3752; A61N 1/3758; A61N 1/3756

USPC ....................................................... 607/36–37
See application file for complete search history.

(56) References Cited

U.S. PATENT DOCUMENTS

| | | | | |
|---|---|---|---|---|
| 3,964,490 A | * | 6/1976 | Nelms | 607/2 |
| 5,133,422 A | * | 7/1992 | Coury et al. | 607/123 |
| 6,163,728 A | * | 12/2000 | Wildon | 607/132 |
| 6,600,479 B1 | * | 7/2003 | Smith et al. | 345/163 |
| 7,032,854 B2 | * | 4/2006 | Marsden | 242/388.1 |
| 7,769,443 B2 | * | 8/2010 | Barolat | 607/3 |
| 8,521,290 B2 | * | 8/2013 | North | 607/37 |
| 8,527,054 B2 | * | 9/2013 | North | 607/38 |
| 2002/0072733 A1 | * | 6/2002 | Flaherty | 604/890.1 |
| 2003/0199948 A1 | * | 10/2003 | Kokones et al. | 607/117 |
| 2005/0021120 A1 | * | 1/2005 | Christopherson et al. | 607/122 |
| 2006/0065774 A1 | * | 3/2006 | Roques et al. | 244/1 TD |
| 2006/0167522 A1 | * | 7/2006 | Malinowski | 607/37 |
| 2007/0156018 A1 | * | 7/2007 | Krauter et al. | 600/102 |
| 2008/0255630 A1 | * | 10/2008 | Arisso et al. | 607/37 |
| 2010/0001116 A1 | * | 1/2010 | Johnson | 242/588 |
| 2011/0060311 A1 | * | 3/2011 | Barolat | 604/523 |
| 2011/0098795 A1 | * | 4/2011 | Mehdizadeh et al. | 607/117 |

* cited by examiner

*Primary Examiner* — Christopher D Koharski
*Assistant Examiner* — Roland Dinga

(57) ABSTRACT

A medical lead screening connector includes a housing, a plurality of lead receptor channels disposed within the housing, a cover hingedly attached to the housing, and a base element rotationally attached to the housing. Each lead receptor channel includes at least two lead receptor contacts. A conductor cable is attached to and extends away from the housing. The base element is configured to reel in the conductor cable upon rotation of the base element.

18 Claims, 5 Drawing Sheets

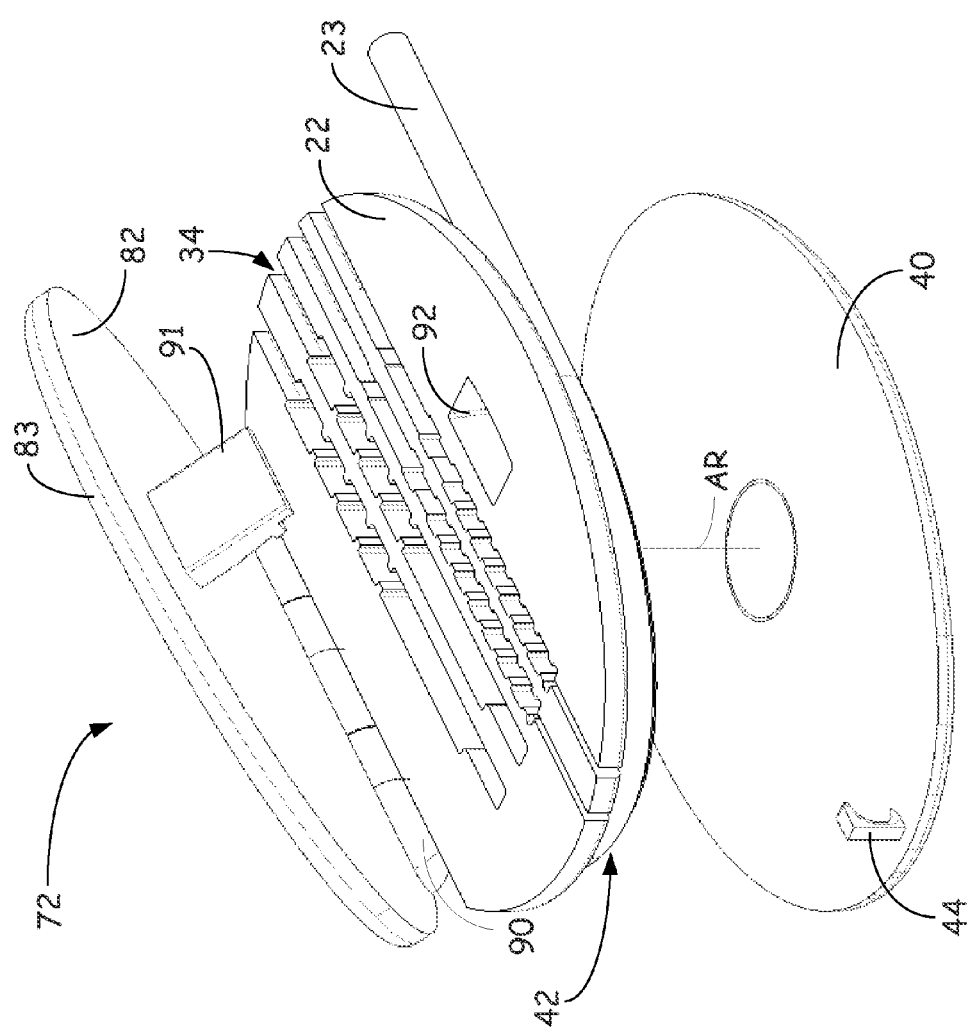

NEUROLOGICAL SCREENING CONNECTOR

The present application claims priority to U.S. Provisional Patent Application No. 61/329,261, filed Apr. 29, 2010, which application is hereby incorporated by reference as if re-written in its entirety.

BACKGROUND

The medical device industry produces a wide variety of electronic and mechanical devices for treating patient medical conditions such as pacemakers, defibrillators, neurostimulators and therapeutic substance delivery pumps. Medical devices can be configured to be surgically implanted or connected externally to the patient receiving treatment. Clinicians use medical devices alone or in combination with therapeutic substance therapies and surgery to treat patient medical conditions. For some medical conditions, medical devices provide the best and sometimes the only therapy to restore an individual to a more healthful condition and a fuller life.

One type of medical device is an implantabhe neurological stimulation system that can be used to treat conditions such as pain, movement disorders, pelvic floor disorders, gastroparesis, and a wide variety of other medical conditions. The neurostimulation system typically includes a neurostimulator, a stimulation lead, and an extension. The neurostimulator can be connected to a stimulation lead that has one or more electrodes to deliver electrical stimulation to a specific location in the patient's body.

The lead and stylet combination are part of an implantable neurostimulation system. The neurostimulation lead is placed in the desired location of the body. The stylet wire and handle combination are used to give the lead stiffness during implantation and to aid in maneuvering the lead into the desired position. Once the lead is believed to be placed in the appropriate position within the body the lead, with or without the stylet, is coupled with a neurostimulation screening cable, which is connected to a neurostimulation screening device. The screening device can be programmed to send different combinations, strengths and frequencies of electrical stimulation to the patient. The screening cable provides a connection to, and electrical pathway between the stimulation lead or percutaneous extension and the neurostimulation screening device. The patient is questioned to determine if the stimulation covers the desired region of the body. Provided results are favorable the patient receives a temporary implant of the stimulation lead system. Either the stimulation lead or percutaneous extension is attached to the screening cable for a trial screening period so the patient can assess the efficacy of the system in normal life settings. The patient can be sent home with an external neurostimulator that sends electrical stimulation to the stimulation lead via the screening cable during the trial period. This trial period can range from 1 to 30 days depending on the physician and the country in which the trial occurs. This trial period is used to access the efficacy of the stimulation therapy for the patient.

BRIEF SUMMARY

The present disclosure relates to a medical lead screening connector. In particular, the present disclosure relates to a medical lead screening connector that includes a number of features that improve screening cable conductor cord management.

In one illustrative embodiment, a medical lead screening connector includes a housing, a plurality of lead receptor channels disposed within the housing, a cover hingedly attached to the housing, and a base element rotationally attached to the housing. Each lead receptor channel includes at least two lead receptor contacts. A conductor cable is attached to and extends away from the housing. The base element is configured to reel in the conductor cable upon rotation of the base element.

In another embodiment, a medical lead screening connector includes a housing including a conductor cable extending away from the housing. The housing includes a groove configured to receive the conductor cable when the conductor cable is wrapped around the housing and a plurality of lead receptor channels are disposed within the housing. Each lead receptor channel includes at least two lead receptor contacts. A cover is hingedly attached to the housing. The lid and housing each have an elliptical cross-sectional area.

These and various other features and advantages will be apparent from a reading of the following detailed description.

BRIEF DESCRIPTION OF THE DRAWINGS

The disclosure may be more completely understood in consideration of the following detailed description of various embodiments of the disclosure in connection with the accompanying drawings, in which:

FIG. 5 is an exploded schematic diagram perspective view of an illustrative screening cable with the cover of the lead screening connector in the open position.

The figures are not necessarily to scale. Like numbers used in the figures refer to like components. However, it will be understood that the use of a number to refer to a component in a given figure is not intended to limit the component in another figure labeled with the same number.

DETAILED DESCRIPTION

Figure 1:
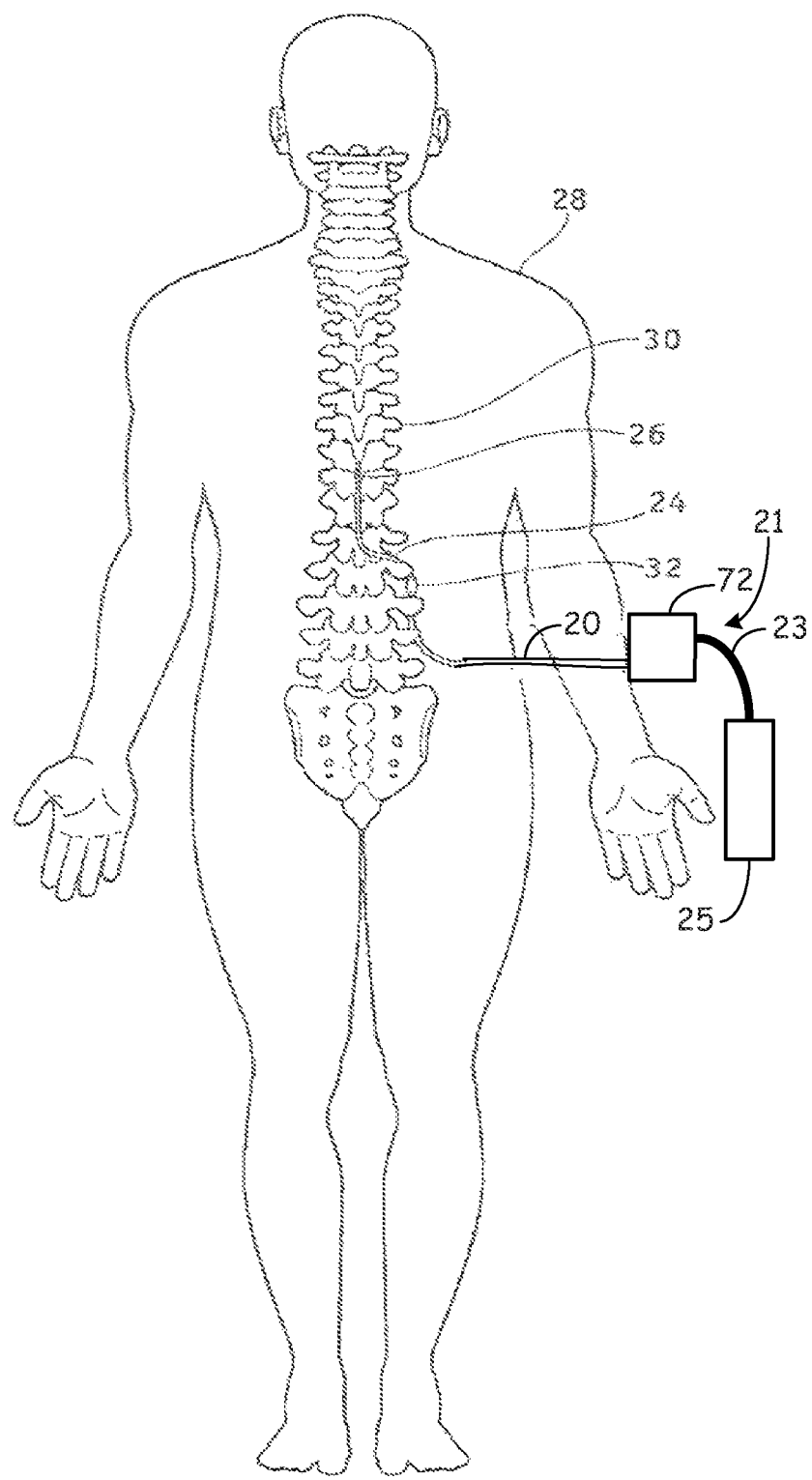
FIG. 1 is a schematic diagram of a neurological lead implanted within a human body or patient.

In the following description, reference is made to the accompanying set of drawings that form a part hereof and in which are shown by way of illustration several specific embodiments. It is to be understood that other embodiments are contemplated and may be made without departing from the scope or spirit of the present disclosure. The following detailed description, therefore, is not to be taken in a limiting sense.

Unless otherwise indicated, all numbers expressing feature sizes, amounts, and physical properties used in the specification and claims are to be understood as being modified in all instances by the term "about," Accordingly, unless indicated to the contrary, the numerical parameters set forth in the foregoing specification and attached claims are approximations that can vary depending upon the desired properties sought to be obtained by those skilled in the art utilizing the teachings disclosed herein.

As used in this specification and the appended claims, the singular forms "a", "an", and "the" encompass embodiments having plural referents, unless the content dearly dictates otherwise. As used in this specification and the appended claims, the term "or" is generally employed in its sense including "and/or" unless the content clearly dictates otherwise. Spatially related terms, including but not limited to, "lower", "upper", "beneath", "below", "above", and "on top", if used herein, are utilized for ease of description to describe spatial relationships of an element(s) to another. Such spatially related terms encompass different orientations of the device in use or operation in addition to the particular orientations depicted in the figures and described herein. For example, if a cell depicted in the figures is turned over or flipped over, portions previously described as below or beneath other elements would then be above those other elements.

As used herein, when an element, component or layer for example is described as being "on" "connected to", "coupled with" or "in contact with" another element, component or layer, it can be directly on, directly connected to, directly coupled with, in direct contact with, or intervening elements, components or layers may be on, connected, coupled or in contact with the particular element, component or layer, for example. When an element, component or layer for example is referred to as begin "directly on", "directly connected to", "directly coupled with", or "directly in contact with" another element, there are no intervening elements, components or layers for example.

The present disclosure relates to a medical lead screening connector. In particular, the present disclosure relates to a medical lead screening cable that includes a number of features that improve the performance and assist in retaining and managing conductor cable of the medical lead screening connector. The screening connector includes a groove circumferentially about the base or housing of the screening connector. The groove is configured to receive and retain the conductor cable extending from the screening connector. The screening connector can have an elliptical cross-sectional area. In some embodiments the screening connector includes a base member that rotates relative to the housing. The conductor cable can be 'reeled' onto the groove via rotation of the base member. While the present disclosure is not so limited, an appreciation of various aspects of the disclosure will be gained through a discussion of the examples provided below.

The teachings presented herein are applicable to any implantable medical device system employing a lead for delivering electrical signals to a tissue of a patient. For example, the system may include a neurostimulator, such as a peripheral nerve stimulator, a spinal cord stimulator, or a deep brain stimulator; a cardiac pacemaker or defibrillator; a gastric stimulator; or the like. It will be understood that the systems and devices described herein may be readily applied to systems employing leads for purposes of screening, sensing, monitoring, recording, or the like.

FIG. 1 is a schematic diagram of a neurological lead 24 implanted within a human body or patient 28. The implanted neurological lead 24 is a medical wire with special insulation. The neurological lead 24 includes one or more insulated electrical conductors with a connector on the proximal end and electrical contacts on the distal end. Some neurological leads are designed to be inserted into a patient percutaneously, and some neurological leads are designed to be surgically implanted. The neurological lead 24 may also be a paddle having a plurality of electrodes. Those skilled in the art will appreciate that any variety of neurological leads 24 may be used.

The neurological lead 24 can be implanted and positioned to stimulate a specific site in the spinal cord 30 or the nervous system. The neurological lead 24 includes one or more electrodes 26 (small electrical contacts) through which electrical stimulation is delivered from a either an external stimulator 25 or an implanted stimulator (not shown) to the targeted neural tissue. The external stimulator 25 or an implanted stimulator can be any "active medical device" or "signal generator" as described above and can be placed external to or in any location within a body cavity or tissue within the body, or on the surface of a patient's skin, as desired.

The external stimulator 25 can be used to test the efficacy of stimulation therapy for the patient before an implantable stimulator is surgically implanted. The external stimulator 25 is used in conjunction with a screening cable 21 which accepts the stimulation lead 24 or lead extension 20 and creates an electrical pathway to the external stimulator 25. The screening cable 21 includes a conductor cable 23 and a distal screening connector 72 that includes pivoting lead receptacles (described below). The conductor cable 23 electrically connects the lead receptacles within the distal screening connector 72 to the external stimulator 25.

The illustrated external stimulator 25 is coupled to a lead extension 20 via the screening cable 21. The lead extension 20 has a proximal end coupled to the screening cable 21, and a lead 24 having a proximal end coupled to a distal end 32 of the lead extension 20 and a distal end of the lead 24 coupled to one or more electrodes 26. In some embodiments, the lead 24 proximal end is coupled to the screening cable 21, without a need for a lead extension. In many embodiments, the screening cable 21 couples to one or two or more leads each having four to eight electrodes. Such a system may also include a physician programmer and a patient programmer (not shown). The external stimulator 25 can be considered to be a signal generator of the type available from Medtronic, Inc, and capable of generating multiple signals occurring either simultaneously or one signal shifting in time with respect to the other, and having independently varying amplitudes and signal widths. The external stimulator 25 can contain a power source and the electronics for sending precise, electrical signals to the patient to provide the desired treatment therapy. While the external stimulator 25, in many embodiments, provides electrical stimulation by way of signals, other forms of stimulation may be used as continuous electrical stimulation.

In many embodiments, the lead 24 is a wire having insulation thereon and includes one or more insulated electrical conductors each coupled at their proximal end to a connector and to contacts/electrodes 26 at its distal end. Some leads are designed to be inserted into a patient percutaneously, and some are designed to be surgically implanted. In some embodiments, the lead 24 may contain a paddle at its distant end for housing electrodes 26. In many embodiments, electrodes 26 may include one or more ring contacts at the distal end of lead 24.

Figure 2:
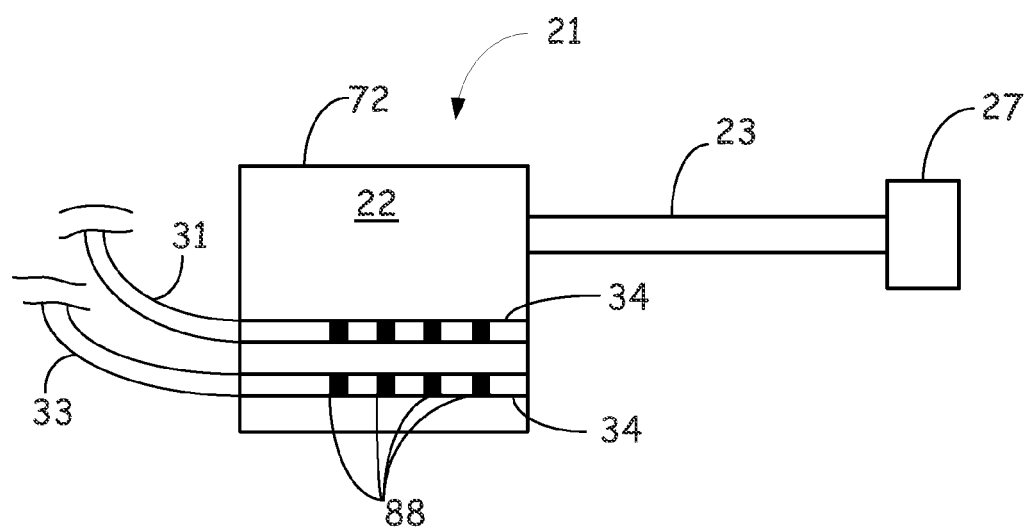
FIG. 2 is a schematic diagram of an illustrative screening cable.

FIG. 2 is a schematic diagram of an illustrative screening cable 21. The screening cable 21 includes a proximal screening connector 27 electrically coupled to lead receptacles 34 in the lead connector housing 22 of the distal screening connector 72. Conductor wires are disposed within the conductor cable 23 electrically coupled the lead receptacles 34 to the proximal screening connector 27. While two lead receptacles are illustrated, it is understood that the distal screening connector 72 can include any number of lead receptacles, as desired. In some embodiments, the distal screening connector 72 can be directly electrically coupled to a lead screening device or programming device (e.g., external stimulation device).

A first implantable medical lead 31 and second implantable medical lead 33 are received in the lead receptacles 34. The lead receptors 34 are configured for receiving the first implantable medical lead 31 and a second implantable medical lead 33. Electrical contacts on the lead 31, 33 mate with electrical contacts 88 within the distal screening connector 72.

The first implantable medical lead 31 and a second implantable medical lead 33 can be a wide variety of medical leads, such as a neurological lead. In some embodiments the medical lead can be a four-conductor neurological lead, a four-conductor extension, a four conductor neurological lead with stylet handle, a four conductor percutaneous extension with stylet handle, an eight-conductor neurological lead, an eight-conductor extension, an eight-conductor neurological lead with stylet handle, and the like.

Figure 3:
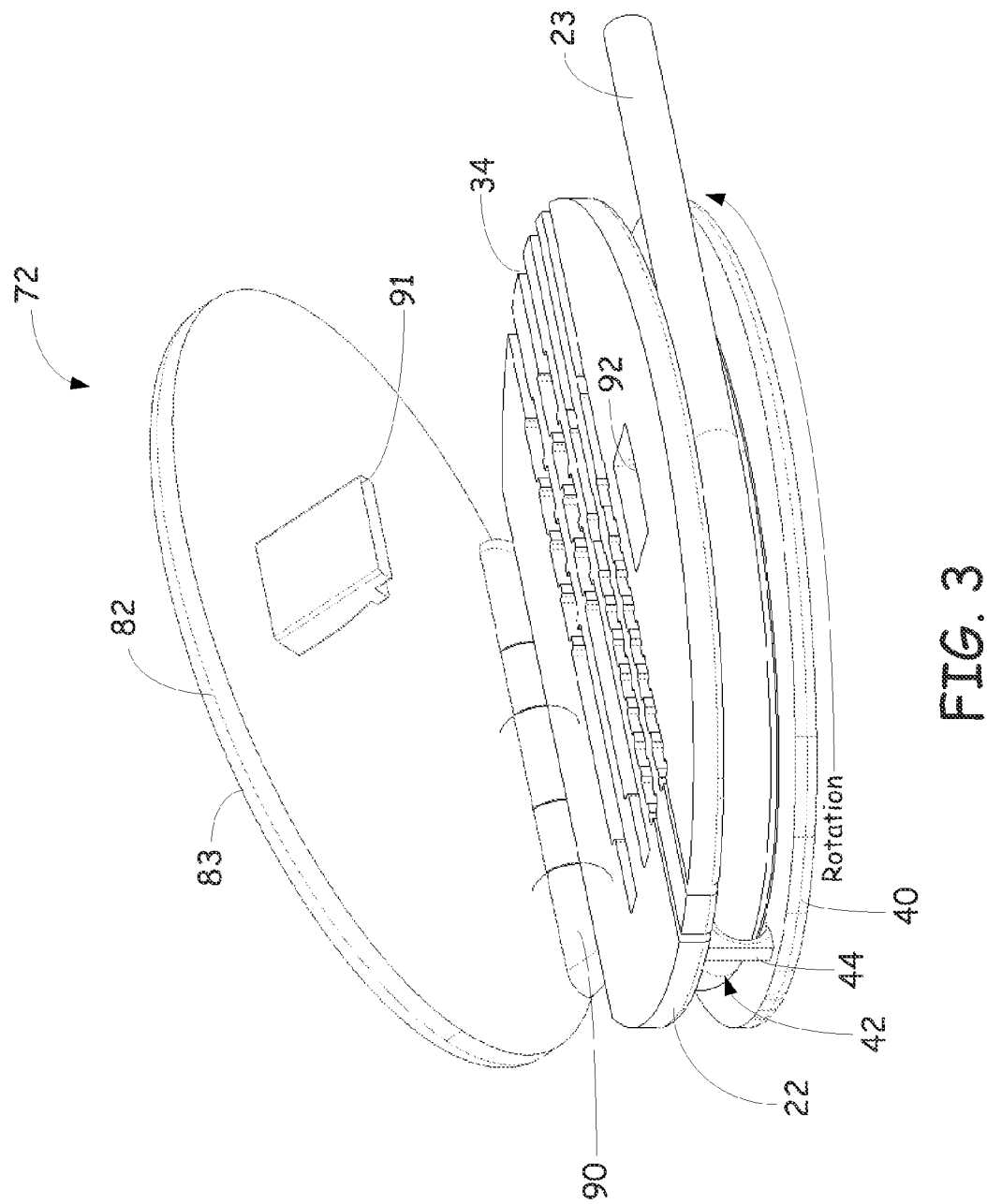
FIG. 3 is a schematic diagram perspective view of an illustrative screening cable with the cover of the lead screening connector in the open position.
Figure 4:
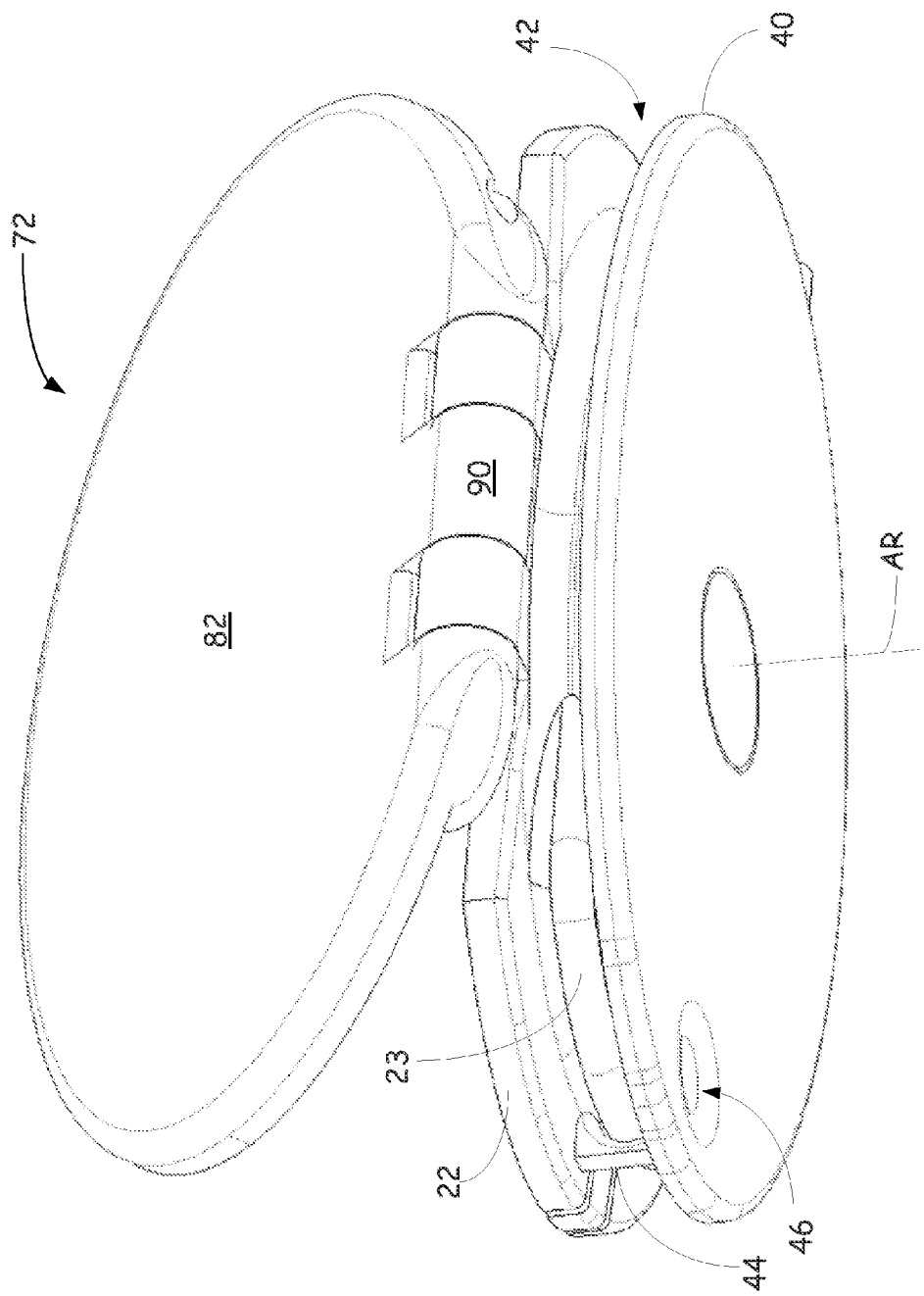
FIG. 4 is a schematic diagram rear view of the illustrative screening cable housing with the cover of the lead screening connector in the open position.

FIG. 3 is a schematic diagram perspective view of an illustrative screening cable with the cover of the lead screening connector in the open position. FIG. 4 is a schematic diagram rear view of the illustrative screening cable housing with the cover of the lead screening connector in the open position. FIG. 5 is an exploded schematic diagram perspective view of an illustrative screening cable with the cover of the lead screening connector in the open position.

The screening cable includes a proximal screening connector electrically coupled to lead receptacles 34 in the lead connector housing 22 of the distal screening connector 72. Conductor wires are disposed within the conductor cable 23 and electrically coupled to lead receptacle 34 receptor contacts to the proximal screening connector 27. While two eight contact lead receptacles and two four contact lead receptacles are illustrated in FIG. 3 to FIG. 5, it is understood that the distal screening connector 72 can include any number of lead receptacles, as desired. The distal screening connector 72 can be directly electrically coupled to a lead screening device or programming device external stimulation device) via the proximal screening connector.

The medical lead screening connector 72 includes a housing 22, a plurality of lead receptor channels 34 that are disposed within the housing 22 and a cover 82 is hingedly attached to the housing 22. Each lead receptor channel 34 includes at least two lead receptor contacts. The lead receptor contacts are configured to mate with the lead contacts when a lead is received in the lead receptor channel 34. The cover 82 can articulate at least 180 degrees between an open position (FIG. 3) and a closed position (not shown). The housing 22 can include the cover 82 hingedly attached to the housing 22 via a hinge 90. The hinge 90 can include a housing hinge portion and a cover hinge portion. The cover 82 has a cover open position for permitting access to the lead receptor channels 34 and a cover closed position for enclosing the lead receptor channels 34 and securing a lead received in the lead receptor channels 34 in the closed position. The cover 82 can include a closing latch element 91 that assists in securing the cover 82 to a closing latch mating element 92 in the housing 22. In many embodiments the cover 82 is constructed from polymer materials and materials that are transparent to visible light. In many embodiments, the lid or cover 82 includes an adhesive layer 83. The adhesive layer 83 can be utilized to adhere the screening connector 72 onto a surface or body portion. The adhesive layer 83 can be disposed on the housing 22 or base 40 also.

The screening connector 72 includes a housing 22, and a plurality of lead receptor channels 34 disposed within the housing 22. Each lead receptor channel 34 includes at least two lead receptor contacts. A conductor cable 23 is attached to the housing 22 and extends away from the housing 22 or base element 40. In many embodiments, a base element 40 is rotationally attached to the housing 22 where the base element 40 is configured to reel in the conductor cable 23 upon rotation of the base element 40. In many embodiments, the screening connector 72 has an elliptical cross-sectional area. In many embodiments, the lid 82, housing 22 and base 40 each have an elliptical cross-sectional area.

In many embodiments the screening connector 72 includes a groove 42 circumferentially disposed about the base 40 or housing 22 of the screening connector. The groove 42 is configured to receive and retain the conductor cable 23. In some embodiments the screening connector 72 includes a base member 40 that rotates relative to the housing 22. The conductor cable 23 can be 'reeled' onto the groove 42 via rotation of the base member 40. The groove 42 can be configured to accept two rotations of the conductor cable 23 into the groove 42. A guide element 44 can be configured with the base element 40 or the housing 22. The guide element 44 is configured to guide the conductor cable 23 into the groove 42 upon rotation of the base element 40.

In some embodiments, the base 40 includes a gripping member 46 to assist in rotating the base element 40. The gripping member 46 can be any useful configuration. The illustrated gripping member 46 is a depression in the base element 40 that is sized and configured to allow an end of a finger to mate with the depression. For example, the screening connector 72 can be connected to leads implanted in a patient and the lid 82 side of the screening connector 72 is adhered to the body of the patient via the adhesive layer 83, for example, and the base element 40 is rotated relative to the housing 22 and cover 82 about the axis of rotation AR utilizing the gripping member 46. The base element 40 can be rotationally connected to the housing 22 via any useful means, such as a shaft or pin, for example.

Thus, embodiments of the NEUROLOGICAL SCREENING CONNECTOR are disclosed. The implementations described above and other implementations are within the scope of the following claims. One skilled in the art will appreciate that the present disclosure can be practiced with embodiments other than those disclosed. The disclosed embodiments are presented for purposes of illustration and not limitation, and the present invention is limited only by the claims that follow.

What is claimed is:

1. A medical lead screening connector comprising:
a housing comprising a groove extending circumferentially about an exterior surface of the housing;
a plurality of lead receptor channels disposed within the housing, each lead receptor channel comprising at least two lead receptor contacts;
a cover hingedly attached to the housing;
a base element rotationally attached to the housing; and
a conductor cable attached to the housing and extending away from the housing, the base element configured to reel in the conductor cable onto the groove upon rotation of the base element.

2. A medical lead screening connector according to claim 1, wherein the cover is formed of a transparent material.

3. A medical lead screening connector according to claim 2, wherein the cover can articulate at least 180 degrees between an open and closed position.

4. A medical lead screening connector according to claim 3, wherein the base comprises a gripping member that assists in rotating the base element.

5. A medical lead screening connector according to claim 4, wherein the gripping member is a depression in the base element that assists in rotating the base element.

6. A medical lead screening connector according to claim 1, wherein the base element comprises a guide element configured to guide the conductor cable into the groove upon rotation of the base element.

7. A medical lead screening connector according to claim 6, wherein the cover comprises an adhesive layer disposed on an outer surface of the cover.

8. A medical lead screening connector according to claim 7, wherein the cover, housing and base each have an elliptical cross-sectional area.

9. A medical lead screening connector according to claim 8, wherein the groove is configured to accept two rotations of the conductor cable into the groove.

10. A medical lead screening connector according to claim 8, wherein the conductor cable electrically connects the lead receptor contacts to a lead screening device.

11. A medical lead screening connector comprising:
a housing comprising a conductor cable extending away from the housing, the housing comprising a groove extending circumferentially about an exterior surface of the housing and the groove receives the conductor cable when the conductor cable is wrapped around the housing;
a plurality of lead receptor channels disposed within the housing, each lead receptor channel comprising at least two lead receptor contacts; and
a base element rotationally attached to the housing; and
a cover hingedly attached to the housing;
wherein the cover and housing each have an elliptical cross-sectional area and the base element is configured to reel in the conductor cable onto the groove upon rotation of the housing relative to the base element.

12. A medical lead screening connector according to claim 11, wherein the cover is formed of a transparent material.

13. A medical lead screening connector according to claim 12, wherein the cover can articulate at least 180 degrees between an open and closed position.

14. A medical lead screening connector according to claim 13, wherein the cover comprises an adhesive layer disposed on an outer surface of the cover.

15. A medical lead screening connector according to claim 14, wherein the groove is configured to accept two rotations of the conductor cable into the groove.

16. A medical lead screening connector according to claim 15, wherein the housing comprises an adhesive layer disposed on an outer surface of the housing.

17. A medical lead screening connector according to claim 16, wherein the conductor cable extends away from the housing at the groove.

18. A medical lead screening connector according to claim 17, wherein the conductor cable electrically connects the lead receptor contacts to a lead screening device.

* * * * *